United States Patent [19]

Jacobus

[11] Patent Number: 5,658,952
[45] Date of Patent: Aug. 19, 1997

[54] 1-[4-(4'-SULFANILYL)PHENYL]UREA AND DERIVATIVES FOR THE TREATMENT OF LEISHMANIASIS

[75] Inventor: David Jacobus, Princeton, N.J.

[73] Assignee: Jacobus Pharmaceutical Co., Inc., Princeton, N.J.

[21] Appl. No.: 520,822

[22] Filed: Aug. 29, 1995

[51] Int. Cl.$^6$ ........................................... A61K 31/17
[52] U.S. Cl. ........................... 514/598; 514/596; 514/597
[58] Field of Search .................................. 514/596, 597, 514/598

[56] References Cited

PUBLICATIONS

HCAPLUS Abstract 1976: 516760, Winkelmann et al. (1976).
HCAPLUS Abstract 1975: 4313, Aichinger et al. (1975).
HCAPLUS Abstract 1985: 100800, O'Doherty et al. (1985).
HCAPLUS Abstract 1981: 71498, Callender et al. (1981).
Pelczar, Jr., et al., *Microbiology* (5th Ed.), McGraw–Hill (1986) pp. 403–405.

*Primary Examiner*—Marianne M. Cintins
*Assistant Examiner*—M. Moezie
*Attorney, Agent, or Firm*—Omri M. Behr, Esq.

[57] ABSTRACT

1-[4-(4'-sulfanilyl)phenyl]urea and its various substituted derivatives can be used to decrease the infectiousness of and reduce the mortality associated with organisms of the genus Leishmania which are responsible for a group of conditions known as Leishmaniasis. This heretofore unrecognized use extends to the known derivatives of ureidodiaminodiphenyl sulfones and includes the novel aryl-ring hydroxylated series of sulfanilylphenylureas of the formula:

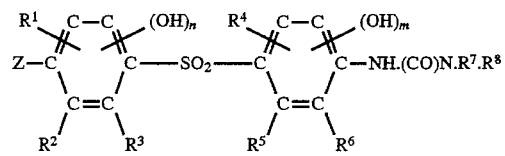

wherein m and n can be the same or different and may each =0 or 1, $R^1$, $R^2$, $R^3$, $R^4$, $R^5$, and $R^6$ are the same or different and are selected from the group consisting of hydrogen, hydroxyl, halo, $C_1$ to $C_6$ straight or branch chain alkyl, halo alkyl, polyhalo alkyl, alkoxy, cyano, amino, alkanoylamino, alkoxycarbonylamino, carboxy, alkoxycarbonyl, carbamoyl, acyl, $R^7$, and $R^8$ are the same or different and are selected from the group consisting of hydrogen, and $C_1$ to $C_6$ straight or branch chain alkyl Z is amino, acylamino, alkoxycarbonylamino, alkylamino, substituted amino or nitro;
or its pharmaceutically acceptable salts.

11 Claims, No Drawings

1-[4-(4'-SULFANILYL)PHENYL]UREA AND DERIVATIVES FOR THE TREATMENT OF LEISHMANIASIS

BACKGROUND OF THE INVENTION

1. Field of the Invention.

The present invention is concerned with a novel pharmaceutical use of the compound 1-[4-(4'-sulfanilyl)phenyl] urea, and derivatives thereof, including the novel ureidosulfones, 1-[4-(4'-sulfanilyl)2-hydroxyphenyl]urea and 1-[4-(4'-sulfanilyl)3-hydroxyphenyl]urea, for its action in treating clinical manifestations associated with the genus Leishmania, resulting in the disorder known as leishmaniasis.

2. Description of the Prior Art.

Leishmaniasis is a debilitating condition caused by any of several species of Leishmania and transmitted by several phlebotomine sandflies. The manifestations may be visceral, mucocutaneous or cutaneous and the strain of the infecting organism and host's immunologic status can influence the clinical signs and symptoms of the parasitic disease. However, leishmaniasis remains a complex disease to treat since so many organ systems of the body can be affected including skin, liver, spleen and bone marrow and in spite of the extensive research which has been carried out in search of effective and well tolerated agents for treatment of its various causal agents and intermediate vectors, few such agents have been discovered. If left untreated, the fatality rate approaches 90%.

No identification of, or description of the utility of 1-[4-(4'-sulfanilyl)phenyl]urea or related ureido compounds for leishmaniasis has appeared, nor has any prediction been made previously as to the probability of the diarylsulfonyl ureas having use in the treatment of said disorders termed leishmaniasis. Based on the biological activities of 1-[4-(4'-sulfanilyl)phenyl]urea and a number of related compounds described by Shigeura et al [Biochemical Pharmacology, 24:687–691 (1975)], no effect was noted on the biosynthesis of DNA, RNA or protein in cultured animal cells, but rather there was demonstrated a marked effect of the previously reported compounds on phosphatidylcholine synthesis. A similar effect was noted for the diaminodiphenylsulfone compound, 4,4'-diaminodiphenylsulfone, but only the ureido compound was substantially effective as an antiviral compound against Marek's disease (ref. U.S. Pat. No. 2,056, 955), suggesting an anticipated differential profile of biological actions for diaminodiphenylsulfones as compared to the substituted ureas.

4,4'-diaminodiphenylsulfone is an established antimalarial and antileprotic agent but the corresponding ureido compound, identified for its activity against coccidial infection (U.S. Pat. No. 2,328,548) has not to date proven commecially useful as a pharmaceutical against other organisms. Whereas 4,4'-diaminodiphenylsulfone has been found to be effective in treating certain infectious and microbial disorders associated with inhibition of folic acid metabolism pathways, comparable potencies have not been observed for the ureido compound. 1-[4-(4'-sulfanilyl)-phenyl]urea, as compared to dapsone and other aminosubstituted diphenyl sulfones has demonstrated the differential effect with the ureidosulfone being far superior to dapsone (×10) and other compounds tested and claimed. [U.S. Pat. Nos. 3,689,671 (1972); 3,702,362 (1972); 3,715,375 (1973); 3,775,403 (1973); 3,775,444 (1973); and 3,786,050 (1974)]. Additionally, U.S. Pat. No. 4,338,334 (1982) discloses the use of the substituted diphenyl sulfones resembling the ureido compounds as agents for treating rheumatoid arthritis, muscular dystrophy, or immune complex diseases, but makes no suggestion of the antileishmania actions of said urea derivatives, nor have data been presented to suggest such action by 1-[4-(4'-sulfanilyl)phenyl]urea, and its derivatives, including the novel series of sulfanilyl-2-hydroxyphenyl and sulfanilyl-3-hydroxyphenylureas.

The clinical literature of the diaminodiphenyl sulfones, as compared to the urea derivatives thereof, has not described therapeutically comparable effects for these two classes of compounds.

Dogra described for the first time, the use of unsubstituted diaminodiphenylsulfone as a treatment for leishmaniasis in the clinic [Dogra, et. al., Intl. J. Dermatol. 25:398–400 (1986)] but no follow-up studies of the use of ureido derivatives, in vivo or in vitro appeared. The continuing interest in the diaminosulfones, but not the ureas, is found in the clinical literature [Dogra, Infection.20:189–191 (1992), "Current therapies for treatment of cutaneous leishmaniasis in India", and Dogra, J. "A double blind study on the efficacy of oral dapsone in cutaneous leishmaniasis Trans. R.Soc. Trop. Med. Hyg. 85:212–13 (1991) and no comparable utility of the ureido derivatives of the sulfones is disclosed or even suggested by those skilled in studies of leishmaniasis and/or its causative pathogens of the family Leishmania.

SUMMARY OF THE INVENTION

The invention is directed to a method of treating infection so as to reduce the level of infection attributable to organisms of the genus Leishmania comprising administering to a patient in need of such treatment a therapeutically effective amount of an active compound of the formula:

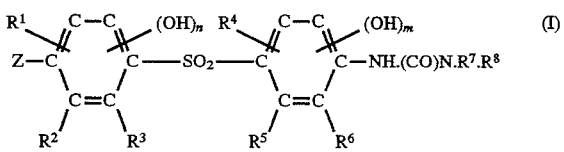

wherein m and n can be the same or different and may each =0 or 1, $R^1$, $R^2$, $R^3$, $R^4$, $R^5$, and $R^6$ are the same or different and are selected from the group consisting of hydrogen, hydroxyl, halo, $C_1$ to $C_6$ straight or branch chain alkyl, halo alkyl, polyhalo alkyl, alkoxy, cyano, amino, acylamino, alkoxycarbonylamino, carboxy, alkoxycarbonyl, carbamoyl, acyl, $R^7$, and $R^8$ are the same or different and are selected from the group consisting of hydrogen, and $C_1$ to $C_6$ straight or branch chain alkyl, Z is amino, substituted amino, including acylamino, alkoxycarbonylamino, alkyl-amino, alkylimino, alkenylamino or nitro; it may also be a substituted amino moiety having the following structure:

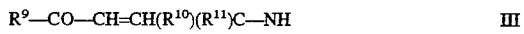

wherein:

$R^9$ is selected from the group consisting of hydrogen, lower alkyl, aralkyl, phenyl or mono or disubstituted phenyl, heterocycloalkyl, heterocycloaryl, containing 1–2 hetero atoms selected independently from the group consisting of O, N, or S;

R[10] and R[11] are the same or different and are selected from the group consisting of hydrogen; lower alkyl, aralkyl, phenyl or mono or disubstituted phenyl, cycloalkyl having 3–9 carbon atoms; and R[12] is selected from the group consisting of R[9] and haloalkyl, as well as the pharmaceutically acceptable salts thereof.

All of the above being within the scope of the compounds useful in the pharmaceutical compositions and methods of treatment of the present invention.

There are also provided certain novel compounds useful as above wherein m, n or both are equal to 1 and Z=amino, especially where R[1] to R[8] are all hydrogen.

PREFERRED EMBODIMENTS OF THE INVENTION

The present invention is concerned with compounds useful for the treatment of leishmaniasis. This biological activity derives from compounds of the formula:

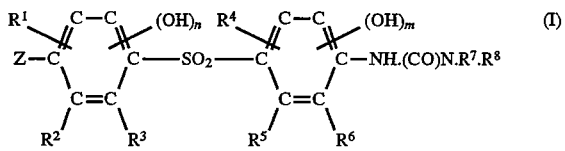

In the preferred compounds of the above formula I, m and n=0 or 1, and can be the same or different;

R[1], R[2], R[3], R[4], R[5], and R[6] are the same or different and are selected from the group consisting of hydrogen, hydroxyl, halo, suitably chloro, fluoro, bromo and iodo, alkyl, haloalkyl, polyhaloalkyl, alkoxy, cyano, amino, alkanoylamino, alkoxycarbonylamino, carboxy, alkoxycarbonyl, carbamoyl, alkanoyl, wherein the prefix alk means a saturated straight or branched carbon chain, suitably as lower alk of 1 to 6 carbon atoms, halo is as defined above and poly means from 2 up to as many such substituents as the moiety will carry, Z is amino, loweralkylimino, loweralkenylamino, loweralkanoylamino, lower-alkoxycarbonylamino, loweralkylamino, or nitro, it may also be a substituted amino moiety having the following sub-structure:

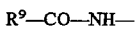 II

 III

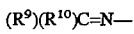 IV

 V wherein:

R[9] is selected from the group consisting of hydrogen lower alkyl, aralkyl, phenyl or mono or disubstituted phenyl, wherein the substituents are selected from the group consisting of chloro, hydroxy, loweralkoxy, and a 3,4-methylenedioxy substituent; heterocycloalkyl, heterocycloaryl, containing 1–2 hetero atoms selected independently from the group consisting of O, N, or S; and a branched alkyl group having 3–9 carbon atoms;

R[10] and R[11] are the same or different and are selected from the group consisting of hydrogen; cycloalkyl having 3–9 carbon atoms; substituted phenyl wherein the substituent is selected from the group consisting of carboxyamino, and nitro; and R[12] is selected from the group consisting of R[9] and haloalkyl, such as halomethyl, having one, two, or three halogens, said halogens being the same or different and being chloro, bromo, fluoro, or iodo, and haloethyl, having 1–5 halogen atoms, being the same or different and defined as above;

Except where differently defined, the prefix alk means a saturated straight or branched carbon chain, suitably as lower alk of 1 to 6 carbon atoms, halo is as defined above and poly means from 2 up to as many such substituents as the moiety will carry.

Also included are the pharmaceutically acceptable salts thereof, including the acid addition salts, such as, but not limited to, for example hydrochloride, hydrobromide, dihydrogen sulfate, esilate, estolate, isetionate, sulfonate, and the corresponding pharmaceutically acceptable phenolate salts of the hydroxy derivatives claimed herein, such as but not limited to, for example sodium, potassium, calcium.

Preferred compounds for use in the pharmaceutical compositions and methods of treatment of the present invention are 1-[4-(4'-sulfanilyl)phenyl]urea;

1-[4-(4'-sulfanilyl)-2-hydroxyphenyl]urea; and

1-[4-(4'-sulfanilyl)-3-hydroxyphenyl]urea

1-[4-(4'-sulfanilyl)-2-hydroxyphenyl]urea and 1-[4-(4'-sulfanilyl)-3-hydroxyphenyl]urea are prepared from the corresponding 5-fluoro-2-nitro-phenol and 2-fluoro-5-nitrophenol, respectively, via a similar synthetic pathway.

The free phenolic group is first converted to the tetrahydropyranyl ether, prefereably run in dihydropyran as the solvent and catalyzed with a mineral acid, preferably hydrochloric acid, which after gently warming for one hour gives the corresponding 2-substituted (fluoronitrophenyloxy) tetra-hydropyran. Commercially available 5-fluoro-2-nitrophenol is used for synthesis of the 1-[4-(4'-sulfanilyl) 3hydroxyphenyl] urea whereas the corresponding known 2-fluoro-5-nitrophenol, readily synthesized from the corresponding fluoronitroaniline, is the starting material for the 1-[4-(4'-sulfanilyl)2-hydroxyphenyl urea.

The tetrahydropyranyl ether of corresponding fluoronitrophenol is reacted with the sodium salt of the known 4-acetaminophenylsulfinic acid, prepared from commercially available 4-acetamino benzenesulfonyl chloride. The 4'-acetamino-(2-tetrahydropyranyloxy)4-nitrodiphenyl sulfone thus obtained is hydrolyzed in an alkaline alcohol/water solution to produce the corresponding 4'-amino-(2-tetrahydropyranyloxy)4-nitrodiphenyl sulfone.

The respective amino-compound is converted in to the corresponding trifluoro-acetamide by heating in a mixture of triethylamine and trifluoroacetic anhydride to give the 4'-trifluoroacetamido-2 or 3-(2-tetrahydropyranyl)oxy-4-nitrodiphenyl sulfone.

Conversion of the protected hydroxy-trifluoroacetamidonitrodiphenyl-sulfone to the tetrahydropyranyl-trifluoracetamidoamino-diphenylsulfone is readily effected in a lower alkanol, preferably methanol, using a Raney nickel catalyst and hydrogen at around 40 psi as has been reported for similar reductions.

The amino compound thus obtained is treated with phosgene followed by gaseous ammonia to yield the corresponding 4'-trifluoroacetamido-2-or-3-(2-tetrahydropyranyl)oxy-4-ureido diphenyl sulfone which can be isolated and treated under mild conditons with dilute mineral acid to remove the protecting groups to obtain the desired 4'-amino-2 or 3-hydroxy-4-ureido-diphenyl sulfone.

For the purposes of treating leishmaniasis, the compounds of Formula I may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection, intraarticular, or infusion techniques in subjects susceptible to leishamania organism infection.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets including but not limited to inert diluents, granulating and disintegrating agents, and lubricating agents; tablets may be uncoated or they may be coated by known techniques to delay disintegration and adsorption in the gastrointestinal tract and thereby provide a sustained action over a longer period.

Aqueous suspensions contain the active materials in admixture with excipients suitable for the manufacture of aqueous suspensions. Such excipients are suspending agents, dispersing or wetting agents. The said aqueous suspensions may also contain one or more preservatives, and oily suspensions may be formulated by suspending the active ingredient in a suitable vegetable oil or in a mineral oil such as liquid paraffin. The oil suspensions may contain a thickening agent, sweetening agents, and flavoring agents may be added to provide a palatable oral preparation. These compositions may be preserved by the addition of an acceptable antioxidant. Dispersible powders and granules suitable for preparation of aqueous suspensions by the addition of water provide the active ingredient in admixture with a dispersing or wetting agent, suspending agent and one or more preservatives. The pharmaceutical compositions of the present invention may also be in the form of oil-in-water emulsions. The oily phase may be a pharmaceutically suitable vegetable oil, arachis oils, or a mineral oil, containing suitable emulsifying agents. The emulsions may also contain sweetening and flavoring agents.

Syrups and elixirs may be formulated with sweetening agents. Such formulations may also contain a demulcent, a preservative and flavoring and coloring agents. The pharmaceutical compositions may be in the form of a sterile injectable preparation, for example as a sterile injectable aqueous or oleaginous suspension. This suspension may be formulated according to the known art using those suitable dispersing or wetting agents and suspending agents.

The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides, fatty acids and other suitable additives of injectables.

The compounds of Formula I may also be administered in the form of suppositories or other formulations such as solutions or suspensions for rectal administration of the drug. Suppositories would have suitable compositions prepared by mixing the drug with a suitable non-irritating excipient which is solid at ordinary temperatures but liquid at the rectal temperature to release the drug.

The daily dosage of the compounds of Formula I may be varied over a wide range from 1.0 to 2,000 mg. Preferably, the compound of Formula I, either by itself, or with a carrier in a pharmaceutical composition, is administered in subdivided doses containing 5, 10, 25, 50, 100, 150, 250 and 500 mg of the active ingredient for the appropriate dosage to the patient to be treated. An effective amount of the drug is ordinarily supplied at a dosage level of from about 0.01 mg to about 50 mg/kg of body weight. Preferably the range is from about 0.1 mg to about 7 mg/kg of body weight.

It will be understood, however, that the specific dose level for any particular patient will depend upon a variety of factors including the activity of the specific compound employed, the age, body weight, general health, sex, diet, time of administration, route of administration, rate of excretion, drug combination and the severity and organ systems affected and in need of therapy.

EXAMPLE 1

2-(2-Fluoro-5-nitrophenyloxy)tetrahydropyran

2-Fluoro-5-nitroaniline (3.2 g) is dissolved in 30 mL $H_2SO_4$ and 80 mL $H_2O$ is mixed with 1.5 g $NaNO_2$ in water below 5° C. After 10 minutes the mixture is filtered, the filtrate added to 400 mL of boiling 50% $H_2SO_4$, and the mixture heated for 15 min., then cooled and the phenol thus obtained, filtered, washed and recrystalized (hexane) to yield 2-fluoro-5-nitrophenol. The phenol thus obtained is taken up in 100 mL of diethyl ether and combined with 17 g dihydropyran, 2 drops of conc. HCl, and the mixture stirred for 1 hour; the mixture is shaken with 5 mL of 10% aq. NaOH; the organic layer is dried ($Na_2SO_4$) and evaporated to yield the 2-(2-fluoro-5-nitrophenyloxy)tetrahydropyran which is used without further purification.

EXAMPLE 2

Acetamidophenylsulfinic Acid

4-Acetamino benzenesulfonyl chloride (150 g) is shaken with a slurry of $Na_2SO_3$ (400 g) in 800 mL $H_2O$. The clear solution which results after about 10 min is acidified with 50% $aq.H_2SO_4$ to pH 0.5, the separated solids filtered off and heated in 2 L $CH_3OH$. The insoluble salts are removed by filtration and the methanolic filtrate concentrated to about 100 mL; The acetamidophenylsulfinic acid thus obtained is filtered off and washed with dry ether.

EXAMPLE 3

4'-Acetamino-2-(2-tetrahydropyranyl)oxy-4-nitro-diphenylsulfone 17.3 g sodium 4-acetamino-benzenesulfinate, prepared in situ from acetamidophenylsulfinic acid and sodium hydride, and 24 g of 2-(2-fluoro-5-nitrophenyloxy)tetrahydropyran, (From Ex. 1), are combined in 100 mL DMSO, and heated at 95° C. for 6 hours. The hot solution is poured over ice, acidified with 2 N HCl, extracted 3 times with a total of 200 mL dichlormethane. The extracts were dried ($Na_2SO_4$) and evaporated. The residual crystals thus obtained are dissolved in 250 mL hot isopropyl alcohol, the solution cooled and diluted with 500 mL ether. The crude crystals, are filtered and recrystalized from ethanol to yield 4'-acetamino-2-(2-tetrahydropyranyl)oxy-4-nitro-diphenylsulfone.

EXAMPLE 4

4'-Amino-2-(2-tetrahydropyranyl)oxy-4-nitrodiphenyl sulfone

4'-Acetamino-2-(2-tetrahydropyranyl)oxy-4-nitrodiphenylsulfone (1.5 g) (Ex. 3) is heated under reflux in 80% aq.ethanol (1000 mL) containing 2 g NaOH for 6 hours. Once the starting material is gone, as measured by thin layer chromatography, the solvent is removed by evaporation the residue washed with water and dried over $Na_2SO_4$ to give 4'-amino-2-(2-tetrahydro-pyranyl)oxy-4-nitrodiphenyl sulfone which is used without further purification.

EXAMPLE 5

4'-Trifluoroacetamido-2-(2-tetrahydropyranyl)oxy-4-nitrodiphenyl sulfone

Amino-3(2-tetrahydropyranyl)oxy-4-nitrodiphenyl sulfone (6.5 g) (Ex 4.) is dissolved in a mixture of triethylamine (50 mL) and trifluoracetic anhydride (20 mL), heated under reflux for 1 hour with protection from moisture, and the solvents removed by evaporation in vacuo, to give a residue which is dissolved in $CHCl_3$ (200 mL), shaken with saturated aq.$NaHCO_3$ (10 mL), and dried over $Na_2SO_4$ to yield 4'-trifluoroacetamido-2-(2-tetrahydropyranyl) oxy-4-nitrodiphenyl sulfone.

EXAMPLE 6

4'-Trifluoroacetamido-2-(2-tetrahydropyranyl)oxy-4-aminodiphenylsulfone

4'-Trifluoroacetamido-2-(2-tetrahydropyranyl)oxy-4-nitrodiphenyl sulfone (5.0 g) (Ex.5) is dissolved in $CH_3OH$ (120 mL) and 0.5 g Raney nickel catalyst added followed by catalytic hydrogenation at about 40 psi in a Parr apparatus for approximately 2 hours, during which time there are taken up 3 Mol of hydrogen). The solution obtained after filtration of nickel catalyst is evaporated in vacuo to give 4'-trifluoroacetamido-2-(2-tetrahydropyranyl)-oxy-4-aminodiphenyl sulfone which is recrystallized from ethanol/toluene and used directly for the next reaction.

EXAMPLE 7

4'-Trifluoroacetamido-2-(2-tetrahydropyranyl)oxy-4-ureidodiphenylsulfone

4'-Trifluoroacetamido-2-(2-tetrahydropyranyl)oxy-4-aminodiphenyl sulfone (4.5 g) (Ex6) is dissolved in dry dioxane (100 mL) and the solution added dropwise over about 0.5 hour to a solution of phosgene (6.0 g) in dioxane (80 mL). The solution is allowed to stand for 2 hours, concentrated in vacuo to dryness, redissolved in dioxane (150 mL) and $NH_3$ gas bubbled into the solution for about 30 minutes. The mixture is stirred for an additional 0.5 hour and the solution evaporated under vacuum to dryness. The 4'-trifluoroacetamido-2-(2-tetrahydropyranyl)oxy-4-ureidodiphenyl sulfone thus obtained is isolated by column chromatography.

EXAMPLE 8

4'-Amino-2-hydroxy-4-ureidodiphenyl sulfone 2.0 g of 4'-trifluoroacetamido-2-(2-tetrahydropyranyl) oxy-4-aminodiphenyl sulfone (Ex. 7) is dissolved in $CH_3OH$ (120 mL), and NaOH (0.22 g) in 20 ml $CH_3OH$ added dropwise with stirring for 1 hour, and the mixture evaporated to dryness in vacuo. To the residue is added 100 ml ethyl acetate and 100 ml water, the organic layer separated, dried over $MgSO_4$ filtered and the filtrate evaporated to dryness to give 4'-amino-2-hydroxy-4-ureidodiphenyl sulfone the crude amino-hydroxy-ureidodiphenyl sulfone which is purified by column chromatography.

EXAMPLE 9

4'-Acetamino-3-(2-tetrahydropyranyl)oxy-4-nitrodiphenylsulfone 17.3 g sodium 4-acetamino-benzenesulfinate, prepared in situ from acetamidophenylsulfinic acid and sodium hydride, and 24 g of 2-(5-fluoro-2-nitrophenyloxy)tetrahydropyran, are combined in 100 mL DMSO, and heated at 95° C. for 6 hours. The hot solution is poured over ice, acidified with 2N HCl, extracted 3 times with a total of 200 mL dichlormethane. The extracts were dried ($Na_2SO_4$) and evaporated. The residual crystals thus obtained are dissolved in 250 mL hot isopropyl alcohol, the solution cooled and diluted with 500 mL ether. The crude crystals, are filtered and recrystalized from ethanol to yield 4'-acetamino-3-(2-tetrahydropyranyl)oxy-4-nitrodiphenylsulfone.

EXAMPLE 10

4'-Amino-3-(2-tetrahydropyranyl)oxy-4-nitrodiphenyl sulfone

4'-Acetamino-3-(2-tetrahydropyranyl)oxy-4-nitrodiphenylsulfone (15 g) (Ex. 3) is heated under reflux in 80% aq.ethanol (1000 mL) containing 2 g NaOH for 6 hours. Once the starting material is gone, as measured by thin layer chromatography, the solvent is removed by evaporation the residue washed with water and dried over $Na_2SO_4$ to give 4'-amino-3-(2-tetrahydropyranyl)oxy-4-nitrodiphenyl sulfone which is used without further purification.

EXAMPLE 11

4'-Trifluoroacetamido-3-(2-tetrahydropyranyl)oxy-4-nitrodiphenyl sulfone

Amino-3-(2-tetrahydropyranyl)oxy-4-nitrodiphenyl sulfone (6.5 g) (Ex 4.) is dissolved in a mixture of triethylamine (50 mL) and trifluoracetic anhydride (20 mL), heated under reflux for 1 hour with protection from moisture, and the solvents removed by evaporation in vacuo, to give a residue which was dissolved in $CHCl_3$ (200 mL), shaken with saturated aq.$NaHCO_3$ (10 mL), and dried over $Na_2SO_4$ to yield 4'-trifluoroacetamido-3-(2-tetrahydropyranyl)oxy-4-nitrodiphenyl sulfone.

EXAMPLE 12

4'-Trifluoroacetamido-3-(2-tetrahydropyranyl)oxy-4-aminodiphenylsulfone

4'-Trifluoroacetamido-3-(2-tetrahydropyranyl)oxy-4-nitrodiphenyl sulfone (5.0 g) (Ex.5) is dissolved in $CH_3OH$ (120 mL) and 0.5 g Raney nickel catalyst added followed by catalytic hydrogenation at about 40 psi in a Parr apparatus for approximately 2 hours, during which time there are taken up 3 Mol of hydrogen). The solution obtained after filtration of nickel catalyst is evaporated in vacuo to give 4'-trifluoroacetamido-3-(2-tetrahydropyranyl)oxy-4-aminodiphenyl sulfone which is recrystallized from toluene and used directly for the next reaction.

EXAMPLE 13

4'-Trifluoroacetamido-3-(2-tetrahydropyranyl)oxy-4-ureidodiphenylsulfone

4'-Trifluoroacetamido-3-(2-tetrahydropyranyl)oxy-4-aminodiphenyl sulfone (4.5 g) (Ex6) is dissolved in dry dioxane (100 mL) and the solution added dropwise over about 0.5 hour to a solution of phosgene (6.0 g) in dioxane (80 mL). The solution is allowed to stand for 2 hours, concentrated in vacuo to dryness, redissolved in dioxane (150 mL) and $NH_3$ gas bubbled into the solution for about 30 minutes. The mixture is stirred for an additional 0.5 hour and the solution evaporated under vacuum to dryness. The 4'-trifluoro-acetamido-3-(2-tetrahydropyranyl)oxy-4-ureidodiphenyl sulfone thus obtained is isolated by column chromatography.

EXAMPLE 14

4'-Amino-3-hydroxy-4-ureidodiphenyl sulfone 2.0 g of 4'-trifluoroacetamido-3-(2-tetrahydropyranyl) oxy-4-aminodiphenyl sulfone (Ex. 7) is dissolved in $CH_3OH$ (120 mL), and NaOH (0.22 g) in 20 ml $CH_3OH$ added dropwise with stirring for 1 hour, and the mixture evaporated to dryness in vacuo. To the residue is added 100 ml ethyl acetate and 100 ml water, the organic layer separated, dried over $MgSO_4$, filtered and the filtrate evaporated to dryness to give 4'-amino-3-hydroxy-4-ureidodiphenyl sulfone the crude amino-hydroxy-ureidodiphenyl sulfone which is purified by column chromatography.

EVALUTION OF ANTILEISHMANIA ACTIVITY IN VITRO

Methods for the growth of leishmania organisms for in vitro screening are well documented and readily carried out by infecting human monocyte-derived macrophages with amastigotes of Leishmania tropica as described by Berman et al [J. D. Berman and L. S. Lee. "Activity of oral drugs against Leishmania tropica in human macrophages in vitro." Am. J. Trop. Med. Hyg. 32:947–951 (1983)] or by growth of amastigotes of L donovani grown in continuous human macrophage cell culture as described by Looke et al [Looker, D. L., Martinez, S., Horton, M. M. and Marr, J. J. 1966. Growth of Leishmania donovani amastigotes in the continuous human macrophage cell line U937: studies of drug efficacy and metabolism. J. Inf Dis 143:323–27.]

The method of Martinez et al [S. Martinez, D. L. Looker, R. L Berens and J J Marr. Am J. Trop. Med. Hyg. 39:250–255 (1988)] provides preferred suspension culture medium methods for evaluation of in vitro activities. HOS-MEM medium [Berens, R. L. and Marr, J. J. 1978. An easily prepared defined medium for cultivation of Leishmania donovani promastigotes. J. Parasitol 64: 160-61] can be used for growth of an aliquot of $1 \times 10^6$ cells which are then treated and cells differentiate into a nondividing monolayer which is infected with $10^7$ spromastigotes. This method changes the medium within two days to medium with specified drug concentrations which can be changed readily and allow for assays within 7 days.

Cells are counted at the end of the experiment and scored as percent infected and compared as to the percent of cells infected under the influence of test drug versus untreated controls. The percent obtained thus serves as an indication of anti-leishmanial activity in vitro and provides significant leads for clinically useful agents.

The test drug was solubilized in water to which a small amount of 0.1N hydrochloric acid had been added.

TABLE 1

Antileishmanial Activity, in vitro
% Survival of Leishmania sp. amastigotes in Human Macrophages[1]

| Compound | Concentration | |
|---|---|---|
| | 10 ug/ml | 20 ug/ml |
| SPU[2] | 50 ± 15 | 38 ± 14 |
| Pentostam | | 26 ± 17 |
| Ketoconazole | 27 ± 10 | |

1. Average percent survival for all L. sp. evaluated; mean of all determinations ± SD;
2. SPU is 1-4(4'-sulfanilyl)phenyl urea

I claim:

1. A method of treating infection so as to reduce the level of infection attributable to organisms of the genus Leishmania comprising administering to a patient in need of such treatment a therapeutically effective amount of an active compound of the formula:

$$R^1 \underset{R^2}{\overset{C-C}{\underset{C=C}{\bigg\rangle}}} (OH)_n \quad \underset{R^3}{\overset{}{\bigg\rangle}} SO_2 \underset{R^5}{\overset{R^4}{\underset{C=C}{\bigg\langle}}} \underset{R^6}{\overset{C-C}{\bigg\rangle}} (OH)_m \underset{R^8}{\overset{R^7}{\bigg\rangle}} NH(CO)N$$

wherein m and n can be the same or different and may each =0 or 1, $R^1$, $R^2$, $R^3$, $R^4$, $R^5$, and $R^6$ are the same or different and are selected from the group consisting of hydrogen, hydroxyl, halo, $C_1$ to $C_6$ straight or branch chain alkyl, halo alkyl, polyhalo alkyl, alkoxy, cyano, amino, alkanoylamino, alkoxycarbonylamino, carboxy, alkoxycarbonyl, carbamoyl, acyl, $R^7$, and $R^8$ are the same or different and are selected from the group consisting of hydrogen, and $C_1$ to $C_6$ straight or branch chain alkyl Z is amino, acylamino, alkoxycarbonylamino, alkylamino, alkylimino, alkenylamino, substituted amino;

or its pharmaceutically acceptable salts.

2. The method of claim 1 wherein

Z is amino, acylamino, alkoxycarbonylamino, alkylamino, alkylimino, alkenylamino; substituted amino having the following structure:

| $R^9$—CO—NH— | II |
| $R^9$—CO—CH=CH($R^{10}$)($R^{11}$)C—NH | III |
| ($R^9$)($R^{10}$)C=N— | IV |
| $R^{12}$—CONH— | V | wherein:

$R^9$ is selected from the group consisting of hydrogen, lower alkyl, alkenyl, aralkyl, phenyl or mono or disubstituted phenyl, heterocycloalkyl, heterocycloaryl, containing 1–2 hetero atoms selected independently from the group consisting of O, N, or S;

$R^{10}$ and $R^{11}$ are the same or different and are selected from the group consisting of hydrogen; lower alkyl, aralkyl, phenyl or mono or disubstituted phenyl, cycloalkyl having 3–9 carbon atoms; and $R^{12}$ is selected from the group consisting of haloalkyl and $R^9$.

3. The method of claim 1 wherein acyl is alkanoyl.

4. The method of claim 3 wherein alkyl contains 1 to 6 carbon atoms as straight and branch chains.

5. The method of claim 1 where Z is amino, loweralkylimino, loweralkenylamino, loweralkanoylamino, loweralkoxycarbonylamino, loweralkylamino, and additionally, substituted amino having the following structure:

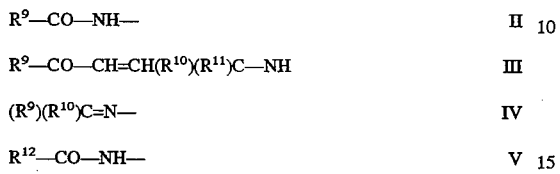

R⁹—CO—NH—   II

R⁹—CO—CH=CH(R¹⁰)(R¹¹)C—NH   III (R⁹)(R¹⁰)C=N—   IV

R¹²—CO—NH—   V wherein:

R$^9$ is selected from the group consisting of lower alkyl, alkenyl, aralkyl, phenyl or mono or disubstituted phenyl, wherein the substituents are selected from the group consisting of chloro; hydroxy, loweralkoxy, and a 3,4-methylenedioxy substituent; heterocycloalkyl, heterocycloaryl, containing 1–2 hetero atoms selected independently from the group consisting of O, N, or S; and a branched alkyl group having 3–9 carbon atoms;

R$^{10}$ and R$^{11}$ are the same or different and are selected from the group consisting of hydrogen; cycloalkyl having 3–9 carbon atoms; substituted phenyl wherein the substituent is selected from the group consisting carboxy- amino, and nitro; and R$^{12}$ is selected from the group consisting of R$^9$, halomethyl, having one, two, or three halogens, said halogens being the same or different and being chloro, bromo, fluoro, or iodo, and haloethyl, haloethyl having 1–5 halogen atoms, being the same or different and defined as above; except where differently defined, alkyl means a saturated straight or branched carbon chain of 1 to 6 carbon atoms, halo is as defined above and poly means from 2 up to as many such substituents as the moiety will carry.

6. The method of claim 1 wherein: m and n=0.

7. The method of claim 1 wherein: n=0, (OH)$_m$ is 2-hydroxy or 3-hydroxy, and

R$^1$, R$^2$, R$^3$, R$^4$, R$^5$ and R$^6$ are hydrogen.

8. The method according to claim 3 wherein (OH)$_m$ is 2-hydroxy, R$_7$ and R$_8$ are hydrogen and Z is amino.

9. The method of claim 1 wherein the active compound is 1-[4-(4'-sulfanilyl)phenyl]urea.

10. The method of claim 1 wherein the active compound is 1-[4-(4'-sulfanilyl)-3-hydroxyphenyl]urea.

11. The method of claim 1 wherein the active compound is 1-[4-(4'-sulfanilyl)-2-hydroxyphenyl]urea.

* * * * *